US00PP14250P29

(12) United States Plant Patent
Hanes

(10) Patent No.: US PP14,250 P2
(45) Date of Patent: Oct. 21, 2003

(54) PETUNIA PLANT NAMED 'WHIP BLUROSE'

(50) Latin Name: *Petunia hybrida*
Varietal Denomination: Whip Blurose

(75) Inventor: Mitchell Eugene Hanes, Morgan Hill, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/389,100

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by colored flowers between red-purple and purple, compact habit and good basal branching.

1 Drawing Sheet

Genus and species: *Petunia hybrida.*
Variety denomination: 'Whip Blurose'.

BACKGROUND OF THE NEW PLANT

The present invention comprises a new and distinct cultivar of petunia, botanically known as *Petunia hybrida,* and hereinafter referred to by the cultivar name 'Whip Blurose'. The new cultivar is asexually reproduced from vegetative cuttings and tissue culture resulting from the cross of the seed/pod parent 99-264-3, a single purple proprietary line that is unnamed and unpatented×'Yellow Horizon', a seed propagated commercial line that is unpatented. 'Whip Blurose' is a product of a planned breeding program intended to create new petunia plants with blue rose colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a three-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Whip Blurose'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light.

Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 10–15 cm.
Width: Approximately 40–55 cm including flowers.
Time to produce a finished flowering plant: 9–11 weeks.
Outdoor plant performance: Full sun, free- flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 4.0–4.5 cm.
Width: 3.0–4.0 cm.
Leaf blade shape: Ovate.
Leaf margin: Entire.
Apex aspect: Acute.
Base aspect: Acuminate.
Leaf color: Upper side; RHS 137B (green); Underside; RHS 138A (green).
Texture: Few short glandular hairs.
Venation: Palmate.
Venation color: RHS 144A (yellow-green).
Petiole length: 1.0–1.2 cm.
Petiole width: 2.0 cm.
Petiole color: RHS 144B (yellow-green).
Petiole texture: Glandular hairs of various sizes.

THE STEM

Length: 40–55 cm.
Diameter: 0.2–0.3 cm.
Internode length: 2.0–5.0 cm.
Color: RHS 144A (yellow-green).
Texture: Long glandular hair.
Stem anthocyanin: None.
Peduncle color: RHS 144A/B (yellow-green).
Peduncle length: 6.5–8.0 cm.
Peduncle diameter: 1.0 cm.
Peduncle texture: Glandular hairs of various sizes.

THE BUD

Shape: Oblong.
Diameter: 0.4–0.5 cm.
Length: 1.5–3.0 cm.
Color at tight bud: RHS 154C (yellow-green) with RHS 178B (greyed-red) veining.

THE FLOWER

Blooming habit: Continuous all through the growing season. Good floriferousness.
Inflorescence type: Flowers solitary in upper leaf axis.
Young flower color: RHS N78A (purple), but brighter; RHS 79A (purple) mid-veins.
Young flower floret diameter: 3.5–4.0 cm.
Mature flower color: Front side, between RHS N78A (purple) and RHS N74A (red-purple), mid-veins RHS N79C (purple), weak minor veining of RHS N78A (purple). Underside, RHS 77B (purple), upper side veining showing through, mid veins RHS 152B (yellow-green).
Corolla color inside: base color close to RHS 78A (purple); heavy veining of RHS 79A (purple).
Corolla tube length: 2.5–2.9 cm.
Corolla outside texture: Glandular hairs of various sizes.
Floret form and number of petals: Funnel form, 5 lobed petals (single) fused at base.
Flower (limb) diameter: 4.5–4.8 cm.
Petal apex shape: Praemorse.
Petal margin: Entire.
Petal waviness (ruffle of petal): Weak.
Petal lobation: Weak.
Petal texture: Papillose.
Calyx: 5, deeply lobed sepals, fused at base.
Sepal color: RHS 137B (green).
Sepal length: 1.7–2.0 cm.
Sepal width: 0.3–0.6 cm.
Sepal shape: Oblong.
Sepal apex: Obtuse.
Sepal texture: Short glandular hairs.
Lastingness of individual blooms: 4–8 days.
Fragrance: None observed.

THE REPRODUCTIVE ORGANS

Stamens: Five, 2 taller and 3 shorter.
Filament color: RHS 11D (yellow), with a RHS 187A (greyed-purple) blotch right under anther.
Pollen color: RHS 202A-B (black).
Pistil: One.
Stigma: RHS 148B (yellow-green).
Style color: RHS 144C (yellow-green).
Fruit seed set: Not observed.

DISEASE AND INSECT RESISTANCE

Not observed.

COMPARISON WITH KNOWN CULTIVARS

Compared to its female parent 99-264-3 in the following ways: The female parent has a flower color that is purple with a yellow throat compared to the blue rose color. The female parent has a more vigorous trailing plant habit. The female parent is later to flower.

Compared to its male parent 'Yellow Horizon' in the following ways: 'Yellow Horizon' has a large yellow flower compared to 'Whip Blurose', which has a small blue rose flower color. 'Yellow Horizon' grows more upright than does 'Whip Blurose'.

I claim:

1. A new and distinct petunia plant as shown and described herein.

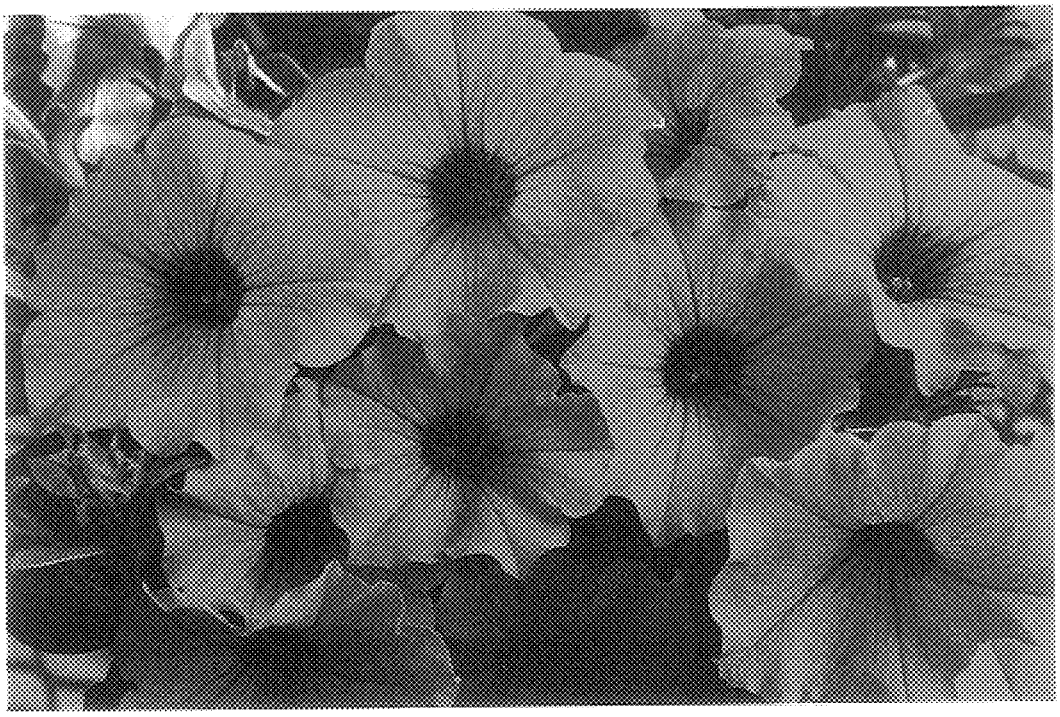

* * * * *